(12) United States Patent
Hellmuth et al.

(10) Patent No.: US 6,204,012 B1
(45) Date of Patent: Mar. 20, 2001

(54) PROTEIN PRODUCTION PROCESS

(75) Inventors: Karsten Hellmuth, Marklohe (DE); Rual Lopez-Ulibarri, Montclair, NJ (US); Anne Françoise Mayer, New York, NY (US); Heinrich Winfried Schlieker, Bloomfield, NJ (US); Adolphus van Loon, Rheinfelden (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/163,052

(22) Filed: Sep. 29, 1998

(30) Foreign Application Priority Data

Oct. 1, 1997 (EP) .................................................. 97117021

(51) Int. Cl.$^7$ .............................. C12P 21/06; C12N 9/14; C12N 15/00; C07H 21/04

(52) U.S. Cl. ..................... 435/69.1; 435/195; 435/252.3; 435/320.1; 435/254.1; 435/255.1; 435/255.5; 435/255.6; 536/23.1; 536/23.2; 530/350

(58) Field of Search .................................. 435/69.1, 195, 435/252.3, 320.1, 23.1, 254.1, 255.1, 255.5, 255.6; 536/23.2; 530/350

(56) References Cited

U.S. PATENT DOCUMENTS 5,667,986 * 9/1997 Goodey et al. ...................... 435/69.1

FOREIGN PATENT DOCUMENTS

| 59543/98 | 1/1998 | (AU) . |
| 173 378 | 3/1986 | (EP) . |
| 183 071 | 6/1986 | (EP) . |
| 299 108 | 1/1989 | (EP) . |
| 0 533 492 A2 | 3/1993 | (EP) . |
| 684 313 | 11/1995 | (EP) . |
| WO 90/03431 | 4/1990 | (WO) . |

OTHER PUBLICATIONS

Fieschko, et al., "Controlled Expression and Purification of Human Immune Interferon from High–Cell–Density Fermentations of *Saccharomyces cerevisiae*," *Biotechnology and Engineering*, vol. 29, pp. 1113–1121 (1987).

Mayer, et al., "An Expression System Matures: A Highly Efficient and Cost–Effective Process for Phytase Production by Recombinant Strains of Hamsenula Polymorpha," *Biotechnology and Bioengineering*, vol. 63, No. 3, pp. 373–381 (1999).

J.M. Cregg et al. Developments in Industrial Microbiology 29, pp. 33–41 (1988).

Y. Sakai et al. J. Bacteriol, 179 pp. 4480–4485 (1997).

Gelissen and K. Melber, Drug Res. 46, pp. 943–948 (1996).

G. Gelissen et al. Gene Expression in Recombinant Microorganisms, Dekker, New York, pp. 195–239 (1994).

Weydemann, P. et al. High–level secretion of hirudin by Hansenula polymorpha, Appl. Microbiol. Biotechnol. 44, pp. 377–385 (1995).

Th. Egli, et al. Regulation of the synthesis of catabolic enzymes, Arch. Microbiol. 124, pp. 115–121 (1980).

Y. Chen et al. J. Chem. Tech. Biotechnol. 67, pp. 143–148 (1996).

L. Pasamontes, et al. Appl. Environ. Microbiol. 63, pp. 1696–1700 (1997).

Ellis et al. Molec. And Cellul. Biol. 1985: pp. 1111–1121.

Ledeboer et al., Nucleic Acid Res. 1985, 3063.

Janowicz et al. Nucleic Acid Res. 1985, 13:3043.

\* cited by examiner

*Primary Examiner*—Tekchand Saidha
(74) *Attorney, Agent, or Firm*—Mark E. Waddell; Stephen M. Haracz; Bryan Cave LLP

(57) ABSTRACT

A method for producing a protein by culturing a cell capable of expressing the protein and which contains a methylotrophic yeast promoter for an enzyme of the methanol metabolic pathway controlling expression of the protein, in a fermentative batch process comprising a batch phase and a feeding phase, under conditions such that dissolved oxygen is continually present in the culture medium throughout the process, and about 1% to about 100% of the carbon source during the feeding phase is a sugar or sugar polymer, which sugar or sugar polymer is provided in such an amount that the sugar or sugar polymer is continually depleted by the cell and therefore is substantially undetectable in the culture medium; and isolating the protein on completion of the feeding phase.

23 Claims, 2 Drawing Sheets

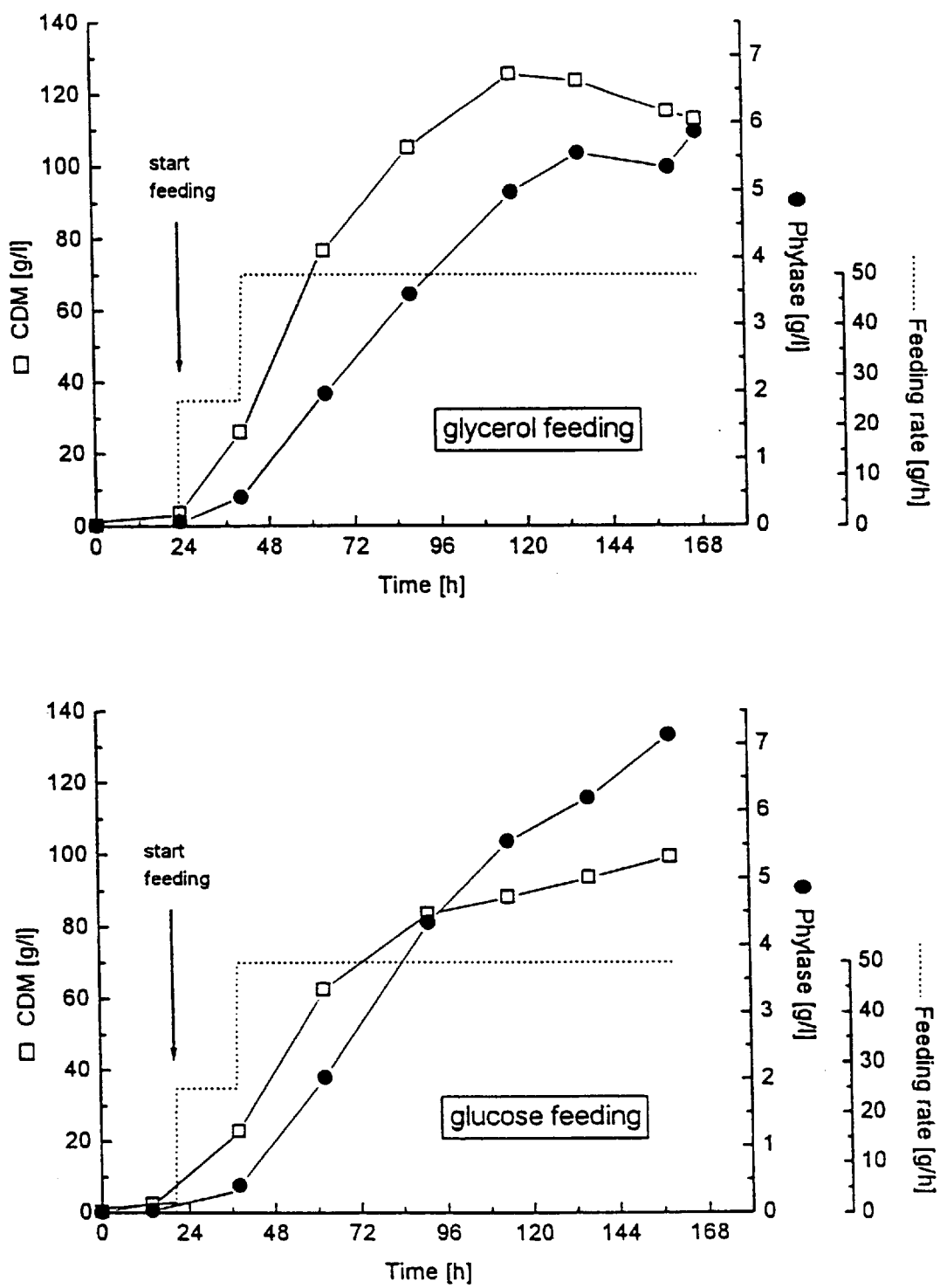
Fig. 1: Time courses for comparative cultivations of H. polymorpha using glycerol or glucose as single carbon source in the feeding phase

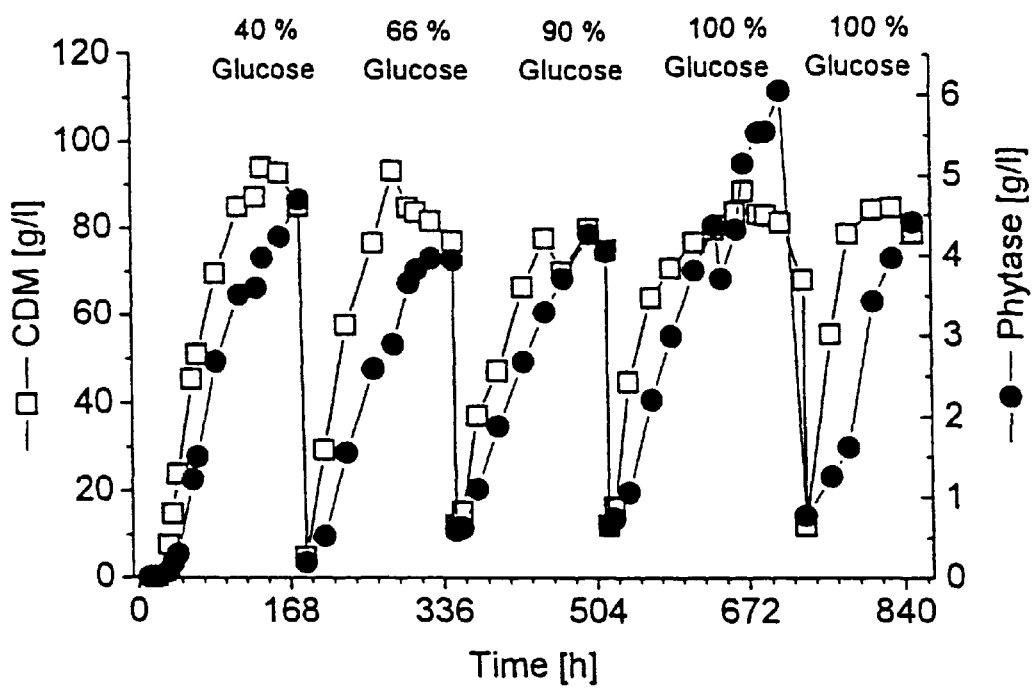
Fig. 2: Repeated fed-batch cultivation cycles with increasing proportions of glucose in the feeding solution

PROTEIN PRODUCTION PROCESS

BACKGROUND OF THE INVENTION

Methylotrophic yeasts are known to provide suitable expression systems for heterologous proteins. *Hansenula polymorpha* and *Pichia pastoris*, for example, are easy to handle host organisms for a wide variety of foreign genes (for reviews see Gelissen & Melber 1996 and Cregg & Madden 1988). The promoters for the enzymes involved in methanol metabolism in these organisms are particularly strong, and these promoters are generally used to control the heterologous expression of proteins (see EP 0173 378, EP 0299 108, EP 0183 071).

The specific carbon source used for cultivation of these organisms has an enormous influence on the regulation of methanol metabolism promoters. Until now, methanol and glycerol have been considered adequate substrates for the methylotrophic yeast expression system, while glucose has been considered inadequate (EP 299 108). During growth on methanol, key enzymes of methanol metabolism in *Hansenula polymorpha* are present in large amounts (Gelissen et al. (1994). Similarly, during growth on glycerol significant levels of the key enzymes methanol oxidase (MOX) and formate dehydrogenase (FMDH) can be detected. Derepression of the MOX and FMDH promoters permits expression of MOX and FMDH during growth on glycerol. However, these enzymes of methanol metabolism are absent in batch cultures if glucose is used as the carbon source (see Gelissen & Melber and EP 0299 108) (in glucose limited chemostat cultures of *Hansenula polymorpha* and *Kloeckera sp.* 2201, FMDH is only produced below growth rates of 0.1 $h^{-1}$ in very small amounts (Egli et al. 1980)). Thus glucose is considered a repressor of the methanol metabolism promoters. These promoters permit only very limited expression of their genes when glucose is the available environmental carbon source.

Therefore, so far nonrepressive carbon sources, e.g. glycerol or methanol, are the standard carbon sources for the heterologous expression of proteins in methylotrophic yeasts. *Hansenula polymorpha* is cultivated for the production of a wide variety of pharmaceutical proteins in a fed batch process either in the single carbon source mode with glycerol or in the two carbon source mode with glycerol and additional methanol (Gelissen & Melber 1996). The common process strategy is described in more details by Weydemann et al. (1995) for the production of hirudin. A process for the production of thrombomodulin with a *Pichia pastoris* strain using also glycerol as a non repressive carbon source is described by Chen et al. (1996).

However, due to the high price of glycerol this process is not cost-effective for the production of low cost proteins like feed or industrial enzymes. Methanol is not a useful alternative due to handling problems caused by its toxicity and volatility. Therefore in the production of low cost proteins, methylotrophic yeast systems are not typically used. Glucose-metabolizing filamentous fungi are the standard expression system. However, these fungi require complex media, form a viscous culture difficult to handle, and produce significant quantities of undesired proteins such as proteases, decreasing yield and making purification of the target protein awkward. Thus the methylotrophic yeast system would be a much preferable production method for low cost proteins if expensive or dangerous substrates were not required.

SUMMARY OF THE INVENTION

Surprisingly, it is now possible to use glucose, glucose-containing compositions or a similar sugar as a carbon source for protein production with a promoter of the methylotrophic yeast methanol metabolic pathway, even though glucose and other monosaccharides are known repressors of such promoters. It has been discovered that this is possible if culture conditions are controlled such that the carbon source is a limiting factor, while oxygen is not.

Therefore it is an object of the present invention to overcome such obstacles and to provide a process for the preparation of an endogenous or heterologous protein by cultivation of a transformed or non-transformed eukaryotic cell which process is characterized therein that a substrate known to be repressive is used as a carbon source, the carbon source is limiting during the feeding phase and there is no continuous oxygen limitation during the whole cultivation; or such a process wherein the protein is an enzyme, especially a feed enzyme, e.g. phytase, cellulase, xylanase or an industrial enzyme, e.g. amylase, protease, invertase, lipase, catalase, cellulase, glucose oxidase, alcohol oxidase, pectinase, naraginase, collagenase, peroxidase or pullalanase; or such a process wherein the cell is methylotrophic and/or is transformed with a DNA sequence comprising a promoter for enzymes involved in the methanol metabolism, e.g. the formate dehydrogenase (FMD or FMDH) promoter, the methanol oxidase (MOX) promoter or the dihydroxyacetone synthase (DAS or DHAS) promoter; or such a process wherein the cell is a methylotrophic yeast, preferably Hansenula, Pichia, Candida or Torulopsis, e.g. *Hansenula polymorpha* or *Pichia pastoris;* or such a process wherein the repressive substrate counts for 1–100%, preferably 40–100% or more preferably 90–100% of the carbon source or is the sole carbon source; or such a process wherein the substrate is a sugar or sugar polymer like mono-, di-, oligo- or poly-saccharide, e.g. glucose, fructose, sucrose, maltose, starch, glycogen, cellulose or dextrose or a sugar containing compound, e.g. molasses, glucose syrups or fructose syrups especially glucose-containing compositions like glucose syrups; or such a process which is effected in form of repeated fed-batches. Furthermore such process is characterized therein that the feeding rate range is limited by the metabolic characteristics of the microorganisms and the mass transfer performance of the bioreactor, in particular for oxygen. Feeding rates are preferentially maintained between the minimum to allow production and the maximum to avoid oxygen limitation in the culture.

Therefore, this invention is directed to a method for producing a protein which comprises culturing a cell capable of expressing said protein and which contains a methylotrophic yeast promoter for an enzyme of the methanol metabolic pathway controlling expression of said protein, in a fermentative batch process comprising a batch phase and a feeding phase, under conditions such that dissolved oxygen is continually present in the culture medium throughout the process, and about 1% to about 100% of the carbon source during the feeding phase is a sugar or sugar polymer, which sugar or sugar polymer is provided in such an amount that the sugar or sugar polymer is continually depleted by the cell and therefore is substantially undetectable in the culture medium; and isolating the protein on completion of the feeding phase.

A BRIEF DESCRIPTION OF THE FIGURES

FIG. 1: Time courses for comparative cultivations of *H. polymorpha* using glycerol or glucose as a single carbon source in the feeding phase.

FIG. 2: Repeated fed-batch cultivation cycles with increasing proportions of glucose in the feeding cycle.

DETAILED DESCRIPTION OF THE INVENTION

"Culturing" in the context of the present invention has its usual meaning a person skilled in the art is familiar with i.e. growing cells which express a desired protein. The specific culture conditions will depend on the cells used and the proteins to be produced and their expression systems. A person skilled in the art of fermentative production of proteins will be familiar with such conditions. Furthermore it is understood that for the practice of the present invention during the short batch phase, namely the growth phase of the cells, a repressive or a non-repressive carbon source, e.g. glucose or glycerol respectively, can be used. During the fed batch phase, which is the production phase of the desired protein, the culturing process is conducted in the manner as provided by the present invention. Thus with the process of this invention, it is possible to use as a carbon source a compound which is known to repress the promoter being used. This repression is overcome by controlling conditions in the feeding phase as described herein. Although any standard medium appropriate to the given circumstances may be used, it has been discovered that with regard to production of *A. fumigatus* phytase with *Hansenula polymorpha*, the media used in Example 1 provides optimal results (the thiamine is optional), when used as indicated in that Example.

Any typical protein may be produced by the method of this invention provided a cell is available which produces the protein, either naturally or by genetic engineering methods. A skilled person will be familiar with techniques for isolating cells which produce desired proteins, obtaining genes encoding such proteins, and manipulating the genes to obtain expression. In addition, public databases make many genes available for use in expression culture. A preferred protein for this production method is an enzyme, especially a feed enzyme such as phytase, cellulase, or xylanase, or an industrial enzyme such as amylase, protease, invertase, lipase, catalase, cellulase, glucose oxidase, alcohol oxidase, pectinase, naraginase, collagenase, peroxidase or pullulanase. These proteins are well known and their genes are available. Examples of promoters which are particularly useful are the FMD or FMDH promoter, the MOX promoter or the DAS or DHAS promoter. These promoters are also known and may be readily obtained by a skilled person (Ellis et al; Ledeboer et al; Janowicz et al; and EP 299 108). Using this method, it is possible to culture the cells in a carbon source that ordinarily represses the promoter, and still obtain good levels of protein expression.

The cell used for protein production is a cell capable of expressing the desired protein. This cell may produce the protein naturally, or may be genetically engineered to produce the protein by well known methods to introduce DNA encoding the protein into the cell in such a way that expression results. Not only does the cell produce the protein, but the DNA encoding the protein is under the control of a promoter for an enzyme of the methanol metabolic pathway from a methylotrophic yeast. This pathway has been well elucidated and will be known to a skilled person (Gellisen, et al. 1994). Methods for assembling such an expression system and introducing it into a host cell are well known. The cell may be designed to express multiple copies of the DNA encoding the desired protein, and may also be designed to express more than one desired protein.

The cell used for protein production may itself be a methylotrophic yeast cell, which is capable of producing the desired protein naturally under the control of one of its methanol metabolic pathway promoters or by introduction of one or more copies of the gene encoding the protein into the cell by any standard method for engineering expression, such that it is under the control of one of its methanol metabolic pathway promoters. Preferred yeast cells are members of the genera Hansenula, Pichia, Candida or Torulopsis, and especially preferred yeast cells are the well known *Hansenula polymorpha* or *Pichia pastoris*. In addition, methylotrophic yeasts of interest for the practice of the present invention are described in EP 173 378, pages 37 and 38. Promoters for use in the method of this invention are obtained from any of the above methylotrophic yeasts. In general methylotrophic yeasts may be obtained by a skilled person based on knowledge of the characteristics of these microorganisms and their habitat. Any promoter from a methylotrophic yeast may be used. Preferred promoters for genes encoding enzymes of the methanol metabolic pathway may be isolated from the yeasts by a skilled person using conventional techniques. Especially preferred promoters are those for the formate dehydrogenase gene, the methanol oxidase gene, and the dihydroxyacetone synthase gene.

The cell used for protein production may also be a eukaryotic cell other than a yeast cell. Any standard eukaryotic host cell is contemplated. The eukaryotic host cell may be engineered by standard methods to contain a methylotrophic yeast metabolic pathway promoter and expresses the protein from one or more copies of its gene under the control of the promoter. Examples of promoters which are particularly useful are the FMD or FMDH promoter, the MOX promoter or the DAS or DHAS promoter, which as noted above are well known. Thus in the case of a process for the production of a heterologous protein, the eukaryotic cell has been transformed by a DNA sequence or a vector comprising a DNA sequence encoding such heterologous protein, e.g. in the examples of the present case, a phytase. A person skilled in the art of molecular biology is familiar with the methods used to prepare such transformed eukaryotic cells, for the specific examples of the present case see EP 684 313 or European Patent Application No. 97810175.6.

The fermentative batch process used in the present method is a well known technique for growing up cells in volume to make proteins. The process is divided into the batch phase, during which the cells start growing, and the feeding, or fed batch, phase, during which the cells continue growing at a controlled growth rate, and express the desired protein. Conditions, equipment and materials for performing fermentative batch processing for any conventional cell are well known. Measurement of various components in the fermenter, such as temperature, pH, dissolved oxygen level, amount of carbon source, and the like, is also well known and accomplished by standard instrumentation. A carbon source for nutrition of the cells is typically provided. The specific carbon source depends on the type of cell and the promoter used. Using this method makes it possible to pair a promoter with a carbon source that ordinarily is considered its repressor, and still produce protein in good yield. Preferred promoters are those derived from the methanol metabolic pathway of methylotrophic yeasts, and it is possible to use sugars or sugar polymers as the carbon source, despite their being known as repressors, rather than the known derepressors glyerol (costly) and methanol (difficult to work with).

The sugar or sugar polymer which is used as the carbon source for protein production is preferably a mono-, di-, oligo- or polysaccharide, such as glucose, fructose, sucrose, maltose, starch, glycogen, cellulose or dextrose. Monosaccharides are in particular known to be repressors as described above. The sugar may be pure, or may be part of a sugar containing composition which is a natural or artificially produced syrup, such as molasses, or glucose or fructose syrup. A particularly preferred sugar is glucose or a glucose-containing composition such as glucose syrup. The sugar or sugar polymer used as the carbon source may make up about 100% of the carbon source used, or as little as about 40%. It is preferably that the sugar or sugar polymer make up about 90% to about 100% of the carbon source, most preferably about 100%.

Dissolved oxygen is present in the culture medium at all times during the feeding phase. A preferable level of dissolved oxygen in the culture medium is from a minimum of about 1% to about 100% saturation, more preferably about 10% to about 100% saturation, and most preferably about 20% saturation. In a particularly preferred method of this invention, the level of dissolved oxygen is about 20% saturation, the sugar is glucose and constitutes about 100% of the carbon source.

In order to practice the claimed method, it is necessary to control conditions during the feeding phase. The batch phase ends and the feeding phase begins when the carbon source in the batch phase is used up and the $pO_2$ increases rapidly The rapid increase in pO2 occurring at the end of the batch phase indicates depletion of the carbon source in the medium, i.e. reaching of carbon limitation conditions. At this point, feeding of the carbon source is started at a rate high enough to allow cell growth and production but low enough to prevent carbon source accumulation in the medium and to ensure that dissolved oxygen is always present in measurable amounts in the medium. This will maintain the carbon limitation condition throughout the cultivation, which is a necessary condition for this invention.

During the feeding phase, the carbon source (e.g. the sugar or sugar polymer) is continually depleted by the cells and therefore is substantially undetectable in the medium using standard instrumentation conventional for this purpose. By this means it is possible to ensure that the carbon source is limiting. In addition, dissolved oxygen should be continually present during the feeding phase, which means that a certain amount (preferably 1% saturation or above) should be continually measurable using standard instrumentation conventional for this purpose. By this means it is possible to ensure that oxygen is not limiting. Specific amounts and feeding rates are provided in the Examples, however these specific amounts apply to the particular batch size and fermenter parameters exemplified. A skilled person will be readily able to manipulate conditions for any given fermentative batch culture in order to bring about such conditions in the feeding phase where dissolved oxygen is continually present and the carbon source is substantially undetectable (i.e. the carbon source is limiting and the oxygen is not limiting). At the end of the feeding phase, which can be experimentally determined as the time point at which the highest process productivity is reached (protein amount per fermentor volume per process time, g·.l/h), the protein is isolated by conventional methods, either from the medium if the protein is secreted, or from the cells if it is not.

The Examples which follow are illustrative and are not intended to limit the invention in any way.

EXAMPLE 1

Production of *A. Fumigatus* phytase with *Hansenula polymorpha* using glycerol or glucose as main carbon source To compare the production of phytase using glycerol or glucose as feeding substrates, two fed batch experiments were carried out in 15 l reactors with a *Hansenula polymorpha* strain containing about 80 copies of the wild-type phytase gene from *Aspergillus fumigatus* (Pasamontes et al., 1997) under the control of the FMD promoter.

Shake flask cultures were started by inoculating 1 ml of a glycerol stock cell suspension maintained at −70° C. in 50 ml medium with the following composition: 30.0 g/l glycerol; 2.5 g/l $KH_2PO_4$; 5 g/l $NH_4H_2PO_4$; 2.25 g/l $MgSO_4.7H_2O$; 2.5 g/l $(NH_4)_2SO_4$; 1.15 g/l KCl; 0.25 g/l NaCl; 0.375 g/l $CaCl_2.2H_2O$; 0.25 mg/l $H_3BO_3$; 0.05 g/l $(NH_4)_2Fe(SO_4)_2.6H_2O$; 4 mg/l $CuSO_4.5H_2O$; 15 mg/l $ZnSO_4.7H_2O$; 20 mg/l $MnSO_4.H_2O$; 0.05 g/l Na-EDTA; 0.5 mg/l $NiSO_4.6H_2O$; 0.5 mg/l $CoCl_2.6H_2O$; 0.5 mg/l $Na_2MoO_4.2H_2O$; 0.5 mg/l KI; 0.05 g/l thiamin.HCl; 0.15 mg/l biotin. They were cultivated at 30° C. and 200 rpm for 24 h, 30 ml were transferred to a second shake flask stage with 300 ml of the same medium, cultivated at 30° C. and 200 rpm for further 24 h.

300 ml of this seed culture were used as inoculum for a 15 l fermenter with 5 l initial medium composed as follows: 10.0 g/l glycerol; 5.0 g/l $KH_2PO_4$; 10 g/l $NH_4H_2PO_4$; 4.5 g/l $MgSO_4.7H_2O$; 5.0 g/l $(NH_4)_2SO_4$; 2.3 g/l KCl; 0.5 g/l NaCl; 0.2 ml/l antifoam; 0.75 g/l $CaCl_2.2H_2O$; 0.5 mg/l $H_3BO_3$; 0.1 g/l $(NH_4)_2Fe(SO_4)_2.6H_2O$; 8 mg/l $CuSO_4.5H_2O$; 30 mg/l $ZnSO_4.7H_2O$; 40 mg/l MnSO4.H2O; 0.1 g/l Na-EDTA; 1.0 mg/l $NiSO_4.6H_2O$; 1.0 mg/l $CoCl_2.6H_2O$; 1.0 mg/l $Na_2MoO_4.2H_2O$; 1.0 mg/l KI; 0.1 g/l thiamin.HCl; 0.3 mg/l biotin. During the whole process temperature, pH, and aeration were kept constant at 30° C., pH 4.6 and 5 l/h, respectively. The pH was controlled by addition of $NH_3$ 25%. Oxygen saturation was maintained at a minimum value of 20% saturation in the reactor by controlling the stirrer speed and the pressure (0–0.5 bar). The complete consumption of the initial glycerol in the medium led to a rapid increase in the $pO_2$ value and indicated the end of the batch phase. At this point, the feeding with 700 g/l solutions of either glycerol or glucose was started. An initial feeding rate of 25 g solution per hour was used for the first 18 h feeding and then the rate was increased to 50 g/h. The culture volume increased due to the feeding of about 6 liters of carbon source solution up to about 11 liters at the end of the cultivation.

In the case of the cultivation fed with glucose, 98% of the whole carbon source metabolized during the process is glucose, and the remaining 2% correspond to glycerol used during the batch phase. During the whole process, no glucose could be quantified in the supernatant.

After 165 h process time, 5.86 g/l phytase were quantified in samples taken from the cultivation with glycerol by using the Bradford method for protein determination. From the cultivation with glucose, samples after 160 h process time contained 7.12 g/l phytase determined by the same method. These results confirm that the repressive effect of glucose can be avoided with a feeding strategy ensuring a strict carbon limitation during the feeding phase. FIG. 1 shows the comparative time course for the cultivations done with glycerol and with glucose as main carbon source.

EXAMPLE 2

Production of *A. Fumigatus* phytase with *Hansenula polymorpha* using sucrose as main carbon source.

In this example, a cultivation was conducted in a 15 l bioreactor using the same strain as that from Example 1. The seed culture and main cultivation conditions were exactly the same as for Example 1, except for the feeding solution, which contained 700 g/l sucrose. During the process, sucrose concentrations in supernatant samples were never higher than 1 g/l, whereas neither glucose nor fructose could be detected in the same samples. After 167 h cultivation time, 5.27 g/l phytase could be measured in the medium by the Bradford method for protein determination.

EXAMPLE 3

Production of *A. Fumigatus* phytase with *Hansenula polymorpha* using glucose as the sole carbon source In this example, a cultivation was conducted with the same strain of Examples 1 and 2 in a 15 l bioreactor. The seed culture was obtained under the same conditions as Examples 1 and 2. The main cultivation was done starting with 5 l initial medium in the bioreactor with the same composition described in Example 1, except that the initial 10 g/l glycerol were substituted by 10 g/l glucose. The feeding solution was composed by 700 g/l glucose, and was added to the cultivation under exactly the same conditions described in Example 1. After 160 h process time, 7.21 g/l phytase could be detected in the medium, measured by the Bradford method.

EXAMPLE 4

Production of *A. Fumigatus* phytase with *Hansenula polymorpha* in a repeated fed batch mode In this example, repeated fed-batch cultivations in a 15 l reactor with the same *Hansenula polymorpha* strain used in Examples 1, 2 and 3 were conducted. For the first cultivation, a seed culture was obtained by inoculating 1 ml of a glycerol stock cell suspension maintained at −70° C. into 300 ml medium with the following composition: 30.0 g/l glycerol; 13.3 g/l $NH_4H_2PO_4$; 3.0 g/l $MgSO_4·7H_2O$; 6.7 g/l $(NH_4)_2SO_4$; 3.3 g/l KCl; 0.33 g/l NaCl; 1.0 g/l $CaCl_2·2H_2O$; 0.67 mg/l $H_3BO_3$; 0.067 g/l $(NH_4)_2Fe(SO_4)_2·6H_2O$; 5.3 mg/l $CuSO_4·5H_2O$; 20 mg/l $ZnSO_4·7H_2O$; 26 mg/l $MnSO_4·H_2O$; 0.067 g/l Na-EDTA; 0.67 mg/l $NiSO_4·6H_2O$; 0.67 mg/l $CoCl_2·6H_2O$; 0.67 mg/l $Na_2MoO_4·2H_2O$; 0.67 mg/l KI; 0.13 g/l thiamin*HCl; 0.4 mg/l biotin. The shake flask was cultivated at 30° C. and 200 rpm for 30 h, 300 ml were used as inoculum for the main culture in a 15 l bioreactor containing: 150.0 g glycerol; 100.0 g $NH_4H_2PO_4$; 22.5 g $MgSO_4·7H_2O$; 50.0 g $(NH_4)_2SO_4$; 25 g KCl; 2.5 g NaCl; 7.5 g $CaCl_2·2H_2O$; 5 mg $H_3BO_3$; 0.5 g $(NH_4)_2Fe(SO_4)_2·6H_2O$; 40 mg $CuSO_4·5H_2O$; 150 mg $ZnSO_4·7H_2O$; 40 mg $MnSO_4·HO_2$; 0.5 g Na-EDTA; 5.0 mg $NiSO_4·6H_2O$; 5.0 mg $CoCl_2·6H_2O$; 5.0 mg $Na_2MoO_4·2H_2O$; 5.0 mg KI; 1 g thiamin·HCl; 3 mg biotin, for an initial volume of 7.5 l medium.

During the whole process temperature, pH and aeration were kept constant at 30° C., 5.0 and 9.0 l/min, respectively. The pH was controlled by addition of $NH_3$ 25%. Oxygen saturation was maintained at a minimum value of 20% saturation in the reactor by controlling the stirrer speed and the pressure (0–0.5 bar). The complete consumption of the initial glycerol in the medium led to a rapid increase in the $pO_2$ value and indicated the end of the batch phase. At this point, feeding was started with a solution containing 40% glucose and 60% glycerol to a total carbon source concentration of 700 g/l. The feeding rate was controlled at 45 g/h during the whole feeding phase.

For the following repeated fed-batch cultivations, 0.5 to 1 l of culture broth from the previous run were maintained in the bioreactor at the process end as inoculum for the next run. New sterile medium containing the same total amount of salts described above but no carbon source was added to the bioreactor up to a defined initial volume. Therefore, there was no batch phase and the feeding was started immediately as described above. Feeding solutions contained a total of 700 g/l carbon source. The different proportions of glycerol and glucose as well as the initial volume were used as given below:

$2^{nd}$ cycle—66% glucose, 34% glycerol, 7.5 l initial volume
$3^{rd}$ cycle—90% glucose, 10% glycerol, 7.5 l initial volume
$4^{th}$ and $5^{th}$ cycles—100% glucose, 5 l initial volume The concentrations of phytase attained at the end of each cycle were 4.7 g/l, 3.9 g/l, 4.3 g/l, 6.0 g/l and 4.4 g/l, respectively for the $1^{st}$ to $5^{th}$ cycles, as shown in FIG. 2. In the $4^{th}$ cycle, a slower, extended feeding mode at the end of the growth phase led to a higher product concentration.

EXAMPLE 5

Production of consensus phytase with *Hansenula polymorpha*

In this example, a strain of *Hansenula polymorpha* containing about 40 copies of a consensus phytase gene (European Patent Application No. 97810175.6) under the control of the FMD promoter was cultivated in a 15 l bioreactor with the same medium and under the same conditions described in Example 1, using a feeding solution containing 700 g/l glucose for the fed-batch phase. After 165 h cultivation time, the phytase concentration in the medium was 13.1 g/l, as determined by the Bradford method.

EXAMPLE 6

Production of *A. fumigatus* phytase with *Hansenula polymorpha* using glucose syrup as the main carbon source In this example, a cultivation was conducted in a 15 l bioreactor using the same strain as that from Example 1. The seed culture and main cultivation conditions were exactly the same as for Example 1, except for the feeding solution, which was a 700 g/l sugar solution done by diluting glucose syrup (containing 95% glucose per total sugars) with tap water. During the process, no glucose could be detected in the medium. After 160 h, 6.76 g/l phytase were measured in the medium by the Bradford method for protein determination.

EXAMPLE 7

Production of *A. fumigatus* phytase with *Hansenula polymorpha* using fructose as the main carbon source In this example, a cultivation was conducted in a 15 l bioreactor using the same strain as that from Example 1. The seed culture and main cultivation conditions were exactly the same as for Example 1, except for the feeding solution, which contained 700 g/l fructose. During the process, no fructose could be detected in the medium. After 160 h, 5.13 g/l phytase were measured in the medium by the Bradford method for protein determination.

Literature

J. M. Cregg and K. R. Madden (1988): Development of methylotrophic yeast, *Pichia pastoris,* as a host system for the production of foreign proteins, Developments in Industrial Microbiology 29, 33–41

Gelissen and K. Melber (1996): Methylotrophic yeast *Hansenula polymorpha* as production organism for recombinat pharmaceuticals, Drug Res. 46, 943–948

G. Gelissen, C. P. Hollenberger, Z. A. Janowicz (1994): Gene expression in methylotrohic yeasts. In: Smith A. (ed): Gene expression in recombinant microorganisms, Dekker, New York, 195–239

Weydemann, P. Keup, M. Piontek, A. W. M. Strasser, J. Schweden, G. Gelissen, Z. A. Janowicz (1995): High-level secretion of hirudin by *Hansenula polymorpha,* Appl Microbiol Biotechnol 44, 377–385

Th. Egli, J. P. Van Dijken, M. Veenhuis, W. Harder, A. Fiechter (1980): Methanol metabolism in yeasts: Regulation of the synthesis of catabolic enzymes, Arch. Microbiol. 124, 115–121

Y. Chen, J. Krol, and D. Freedman (1996): Continuous production of Thrombomodulin from a *Pichia pastoris* fermentation, J. Chem. Tech. Biotechnol. 67, 143–148

L. Pasamontes, M. Haiker, M. Wyss, M. Tessier, A. P. G. M. Van Loon (1997): Gene cloning, purification, and characterization of a heat-stable phytase from the fungus *Aspergillus fumigatus,* Appl. Environ. Microbiol. 63, 1696–1700

Ellis et al., Molec. and Cellul. Biol. 1985: 1111–21

Ledeboer et al., Nucleic Acid Res. 1985 3063

Janowicz et al., Nucleic Acid Res. 1985 13:3043

What is claimed is:

1. A method for producing a desired protein which comprises culturing a cell capable of expressing the protein comprising a nucleic acid sequence encoding the desired protein operably linked to a methylotrophic yeast promoter having an activity for an enzyme of the methanol metabolic pathway and controlling expression of the desired protein, in a fermentative batch process comprising a batch phase and a feeding phase under conditions such that dissolved oxygen is continually present in the culture medium throughout the process, and about 1% to about 100% of the total carbon source present in the feeding phase is a repressive sugar or a repressive sugar polymer, which is provided in such an amount that the repressive sugar or repressive sugar polymer is continually depleted by the cell and therefore substantially undetectable in the culture medium; and isolating the protein on completion of the feeding phase by collecting and purifying the desired protein from the culture medium.

2. A method of claim 1 wherein the protein is an enzyme.

3. A method of claim 2 wherein the protein is phytase, cellulase, xylanase, amylase, protease, invertase, lipase, catalase, cellulase, glucose oxidase, alcohol oxidase, pectinase, naraginase, collagenase, peroxidase or pullulanase.

4. A method of claim 1 wherein the cell is a methylotrophic yeast cell.

5. A method of claim 4 wherein the yeast cell is a Hansenula, Pichia, Candida or Torulopsis cell.

6. A method of claim 5 wherein the yeast cell is *Hansenula polymorpha* or *Pichia pastoris.*

7. A method of claim 1 wherein the promoter is the formate dehydrogenase promoter, the methanol oxidase promoter or the dihydroxyacetone synthase promoter.

8. A method of claim 1 wherein the cell is eukaryotic host cell which has been engineered to contain the methylotrophic yeast promoter.

9. A method of claim 7 wherein the cell is eukaryotic host cell which has been engineered to contain the methylotrophic yeast promoter.

10. A method of claim 1 wherein the sugar or sugar polymer is a mono-, di-, oligo- or polysaccharide.

11. A method of claim 10 wherein the sugar or sugar polymer is glucose, fructose, sucrose, maltose, starch, glycogen, cellulose or dextrose.

12. A method of claim 11 wherein the sugar is glucose.

13. A method of claim 1 wherein the sugar is in a sugar containing composition which is a natural or artificially produced syrup.

14. A method of claim 13 wherein the sugar containing composition is molasses, glucose syrup, or fructose syrup.

15. A method of claim 14 wherein the sugar containing composition is glucose syrup.

16. A method of claim 1 wherein the sugar or sugar polymer makes up about 40% to about 100% of the carbon source.

17. A method of claim 16 wherein the sugar or sugar polymer makes up about 90% to about 100% of the carbon source.

18. A method of claim 17 wherein the sugar or sugar polymer makes up about 100% of the carbon source.

19. A method of claim 18 wherein the sugar or sugar polymer is glucose.

20. A method of claim 1 wherein the dissolved oxygen is present in the culture medium at a level of from about 1% to about 100% saturation.

21. A method of claim 20 wherein the dissolved oxygen is present in the culture medium at a level of from about 10% to about 100% saturation.

22. A method of claim 21 wherein the dissolved oxygen is present in the culture medium at a level of about 20% saturation.

23. A method of claim 19 wherein the dissolved oxygen is present in the culture medium at a level of about 20% saturation.

* * * * *